(12) United States Patent
Chen et al.

(10) Patent No.: US 10,369,049 B1
(45) Date of Patent: Aug. 6, 2019

(54) PROBES HAVING FIBER TAPER AND FLUID COLLECTION CHANNEL FOR OPHTHALMIC LASER TREATMENT

(71) Applicant: IRIDEX CORPORATION, Mountain View, CA (US)

(72) Inventors: Howard Chen, San Jose, CA (US); George Marcellino, Santa Cruz, CA (US)

(73) Assignee: IRIDEX Corporation, Mountain View, CA (US)

( * ) Notice: Subject to any disclaimer, the term of this patent is extended or adjusted under 35 U.S.C. 154(b) by 0 days.

(21) Appl. No.: 15/999,167

(22) Filed: Aug. 17, 2018

(51) Int. Cl.
| | |
|---|---|
| A61F 9/008 | (2006.01) |
| A61F 9/007 | (2006.01) |
| A61B 18/22 | (2006.01) |
| A61F 9/009 | (2006.01) |

(52) U.S. Cl.
CPC .......... *A61F 9/00781* (2013.01); *A61B 18/22* (2013.01); *A61F 9/009* (2013.01); *A61F 9/00821* (2013.01); *A61B 2018/2205* (2013.01); *A61F 2009/00865* (2013.01); *A61F 2009/00868* (2013.01); *A61F 2009/00872* (2013.01); *A61F 2009/00891* (2013.01)

(58) Field of Classification Search
CPC combination set(s) only.
See application file for complete search history.

(56) References Cited

U.S. PATENT DOCUMENTS

| | | |
|---|---|---|
| 2,033,397 A | 3/1936 | Frances |
| 5,372,595 A | 12/1994 | Gaasterland et al. |
| 6,454,763 B1 | 9/2002 | Motter et al. |
| 8,588,268 B2 | 11/2013 | Boutoussov et al. |
| 9,820,883 B2 | 11/2017 | Berlin |
| 9,835,795 B2 | 12/2017 | Thomsen et al. |
| 2010/0076419 A1 | 3/2010 | Chew et al. |
| 2014/0121653 A1 | 5/2014 | Abe et al. |
| 2015/0374539 A1 | 12/2015 | Buzawa et al. |

(Continued)

FOREIGN PATENT DOCUMENTS

| | | |
|---|---|---|
| SU | 508984 | 8/1979 |

OTHER PUBLICATIONS

Allingham et al., "Probe Placement and Power Levels in Contact Transscleral Neodymium:YAG Cyclophotocoagulation", Arch Ophthalmol, vol. 108, May 1990, pp. 738-742.

(Continued)

*Primary Examiner* — Scott Luan
(74) *Attorney, Agent, or Firm* — Kilpatrick Townsend and Stockton LLP (57) ABSTRACT

A treatment probe for treating an eye of a patient includes an elongate body that defines a handle and a treatment fiber that is housed within the elongate body. The treatment fiber is configured to deliver treatment light energy to the eye. A contact member is disposed on an end of the elongate body. The contact member has a contact surface for positioning on a surface of the eye, two side edges that are positioned on opposite sides of the contact surface, and a fluid channel. The contact surface conforms to the shape of the eye's sclera and the two side edges are shaped to direct fluid that is present on the surface of the eye toward the fluid channel when the contact member is moved laterally across the surface of the eye. The fluid aggregates within the fluid channel and contacts a distal end of the treatment fiber.

33 Claims, 8 Drawing Sheets

(56) References Cited

U.S. PATENT DOCUMENTS

2016/0074672 A1     3/2016   Schomacker et al.
2017/0000648 A1     1/2017   Chabrier et al.

OTHER PUBLICATIONS

Beckman et al., "Transscleral Ruby Laser Irradiation of the Ciliary Body in the Treatment of Intractable Glaucoma", Tr. Am. Acad. Ophth. & Otol., vol. 76, Mar.-Apr. 1972, pp. 423-436.
Schuman et al., "Laser Cyclophotocoagulation", International Ophthalmology Clinics, vol. 30, No. 2, Spring 1990, pp. 111-119.

PROBES HAVING FIBER TAPER AND FLUID COLLECTION CHANNEL FOR OPHTHALMIC LASER TREATMENT

BACKGROUND

The present invention is directed generally to medical devices, systems, and methods, particularly for treatment of an eye. In particular, embodiments of the present invention are directed toward contact probes for the delivery of laser energy, and more particularly to contact probes that are used for lowering the intraocular pressure (IOP) in human eyes afflicted with glaucoma. Even more specifically, the present invention is directed toward laser therapy for lowering IOP in glaucomatous eyes via transconjunctival/transcleral ab-externo treatment with infrared laser energy directed to the ciliary body and pigmented ciliary epithelium, pars plicata, and/or the posterior portion of the pars plicata para plana interface.

Glaucoma is a leading cause of blindness. Glaucoma involves the loss of retinal ganglion cells in a characteristic pattern of optic neuropathy. Untreated glaucoma can lead to permanent damage of the optic nerve and resultant visual field loss, which can progress to blindness. The loss of visual field due to glaucoma often occurs gradually over a long time and may only be recognized when the loss is already quite advanced. Once lost, this damaged visual field can never be recovered.

Raised intraocular pressure (IOP) is a significant risk factor for developing glaucoma. IOP is a function of production of aqueous humor by the ciliary body of the eye and its drainage through the trabecular meshwork and all other outflow pathways including the uveoscleral pathway. Aqueous humor is a complex mixture of electrolytes, organics solutes, and other proteins that supply nutrients to the non-vascularized tissues of the anterior chamber of the eye. It flows from the ciliary bodies into the posterior chamber of the anterior segment, bounded posteriorly by the lens and the ciliary zonule and bounded anteriorly by the iris. Aqueous humor then flows through the pupil of the iris into the anterior chamber, bounded posteriorly by the iris and anteriorly by the cornea. In the conventional aqueous humor outflow path, the trabecular meshwork drains aqueous humor from the anterior chamber through the trabecular meshwork exiting into the Schlemm's canal into scleral plexuses and the general venous blood circulation. In open angle glaucoma there is reduced flow through the trabecular meshwork. In angle closure glaucoma, the iris is pushed forward against the trabeular meshwork, blocking fluid from escaping.

Uveoscleral outflow is an accessory outflow and accounts from 10-20% of total aqueous humor outflow. Enhancing uveocleral outflow is assuming a growing importance in the management of glaucoma. In uveoscleral outflow, aqueous humor enters the ciliary muscles from the anterior chamber and exits through the supraciliary space and across the anterior or posterior sclera. Uveoscleral outflow contributes significantly to total aqueous humor outflow with a reduction in intraocular pressure.

Currently, glaucoma therapies aim to reduce IOP by either limiting the production of aqueous humor or by increasing the outflow of aqueous humor. Medications such as beta-blockers, carbonic anhydrase inhibitors, etc., are used as the primary treatment to reduce the production of aqueous humor. Medications may also be used as the primary therapy to increase the outflow of the aqueous humor. Miotic and cholinergic drugs increase the trabecular outflow, while prostaglandin drugs, for example, Latanoprost and Bimatoprost, increase the uveoscleral outflow. These drugs, however, are expensive and may have undesirable side effects, which can cause compliance-dependent problems over time especially when more than one drug is prescribed.

Surgery may also be used to increase the outflow or to lower the production of aqueous humor. Laser trabeculoplasty is the application of a laser beam over areas of the trabecular meshwork to increase the outflow. Cyclocryotherapy and laser cyclophotocoagulation are surgical interventions over the ciliary processes to lower the production of aqueous humor. Although they may be effective, these destructive surgical interventions are normally used as a last resource in the management of glaucoma due to the risk of the severe complication of phthisis bulbi. Other adverse side effects of cyclodestructive surgical procedures may include temporary or permanent mydriasis (pupil dilation), ocular hypotony, inflammation of the anterior eye segment, which may be associated with an increased incidence of macula complications, and loss of best corrected visual acuity. Still other adverse side effects include transient hyphaema and exudates in the anterior chamber, uveitis, and necrotizing scleritis.

In laser transscleral cyclophotocoagulation, a continuous wave (CW) of high intensity infrared laser energy is directed toward selected portions of the pars plicata region of the ciliary body, structures under the scleral layers and the overlying conjunctiva. Selected portions of the ciliary body and related processes are permanently destroyed, thereby decreasing the overall production of aqueous humor. Laser energy may be directed through air to a patient seated at a special slit lamp. Alternatively, laser energy may be delivered through the use of fiber optic hand pieces placed in contact with the patient's eyeball. In both laser energy delivery methods, however, accurately and repeatedly directing a laser beam a subsurface non-visible target such as the ciliary body can be challenging for a surgeon. Thus, contact hand piece probes (for example, the G-Probe available through IRIDEX Corporation of Mountain View, Calif. and described in U.S. Pat. No. 5,272,595, the full disclosure of which is incorporated herein by reference in its entirety) have been designed to facilitate the aiming of a laser toward the pars plicata region of the ciliary body. The G-Probe, for example, has special contours that facilitate consistent placement and aiming of the probe relative to external landmark structures of the eye (e.g. limbus), thereby guiding the laser light energy to the correct target tissue, thus likely decreasing the likelihood of adverse events and increasing the likelihood of favorable clinical responses.

BRIEF SUMMARY

The embodiments described herein provide improved probes that are configured to treat the eye for various purposes, including the treatment of Glaucoma. According to one aspect, a treatment probe for treating an eye of a patient includes an elongate body that defines a handle having a proximal end and a distal end and a treatment fiber that is housed in the elongate body and that is configured to deliver treatment light energy to the eye from a distal end of the treatment fiber. The treatment probe also includes a contact member that is disposed on an end of the elongate body. The contact member includes a contact surface for positioning on a surface of the eye, two side edges that are positioned on opposite sides of the contact surface, and a fluid channel. The contact surface is shaped to conform to the shape of the eye's sclera and the two side edges are shaped to direct fluid that is present on the surface of the eye toward the fluid channel when the contact member is moved laterally across the surface of the eye. The fluid is directed toward the fluid channel so that the fluid aggregates within the fluid channel and contacts the distal end of the treatment fiber.

The two side edges of the contact member are typically angled or tapered toward the fluid channel so that a width of the contact surface is narrowest adjacent the fluid channel. The contact surface typically has an hourglass or bowtie configuration that is configured to funnel the fluid toward the fluid channel to aggregate the fluid within the fluid channel. The contact member has a top end and a bottom end that are positioned on opposite ends of the two side edges and the top end may have a greater width than the bottom end. The distal end of the treatment fiber is typically centered within the fluid channel. The fluid channel typically has an axial depth from the contact surface of between 3 µm and 300 µm.

In some embodiments, the distal end of the treatment fiber includes an angle or bias cut. The angle or bias cut is configured to bend the treatment light energy toward the eye so that the treatment light energy is delivered at a more perpendicular angle relative to the eye. In some embodiments, a fiber taper element is coupled with the distal end of the treatment fiber. The fiber taper element typically has a larger egress diameter than an ingress diameter and is configured to reduce a divergence angle of a light beam that is emitted from the treatment fiber. The fiber taper element may have a conical frustum shape. The ingress diameter may be between about 50 and 100 µm and the egress diameter may be between about 600 and 1000 µm.

The contact surface of the treatment probe may have a reference structure that is alignable with a reference feature of the eye, typically the limbus—i.e., the junction of the iris and sclera. The reference structure of the contact surface may be an edge of the contact surface that is separated from the distal end of the treatment fiber by between 1.5 mm and 4 mm, and more commonly 2 mm or 3 mm. The treatment probe may be configured so that when the contact surface is positioned on the surface of the eye, the treatment probe is oriented angularly offset from an optical axis of the eye such that the treatment light energy is delivered angularly offset from the optical axis. The treatment probe may be configured to deliver a plurality of pulses of the light energy to the eye to induce a therapeutic response, such as coagulating tissue of the eye and/or destroying ciliary epithelial tissue. The treatment light energy is typically a laser beam, but in some instance may be, or may include, a light emitting diode (LED).

According to another aspect, a method of treating an eye of a patient includes providing a treatment probe that has an elongate body, a treatment fiber that is housed in the elongate body, and a contact member that is disposed on an end of the elongate body. The contact member has a contact surface, two side edges that are positioned on opposite sides of the contact surface, and a fluid channel. The method also includes positioning the contact surface of the contact member on a surface of the eye and moving the contact member laterally across the surface of the eye. The method further includes delivering treatment light energy from a distal end of the treatment fiber to treat tissue of the eye. The contact surface is shaped and sized to conform to the shape of the eye's sclera and the two side edges are shaped to direct fluid that is present on the surface of the eye toward the fluid channel as the contact member is moved laterally across the surface of the eye. The fluid is directed toward the fluid channel in order to aggregate fluid within the fluid channel and thereby wet the distal end of the treatment fiber with the fluid.

The method may include treating a ciliary process of the eye with the treatment light energy. The method may also include applying an irrigation fluid to the surface of the eye. In such instances, the fluid that is directed toward the fluid channel includes the irrigation fluid. Delivering treatment light energy from the distal end of the treatment fiber may include delivering a plurality of pulses of the light energy so as to induce a therapeutic response with or without coagulating the tissue of the eye. The plurality of pulses may be delivered while the contact member is moved laterally across the surface of the eye.

In some embodiments, the method may additionally include positioning the contact surface on the surface of the eye so that the treatment probe is oriented angularly offset from the optical axis. In such embodiments, the treatment light energy may be delivered angularly offset from the optical axis. Positioning the contact surface on the surface of the eye may include positioning a reference structure of the contact surface in alignment with a reference feature of the eye, such as the limbus. In such instances, the reference structure of the contact surface may be an edge of the contact surface that is separated from the distal end of the treatment fiber by between 1.5 mm and 4 mm, and more commonly 2 mm or 3 mm.

The two side edges of the contact member are typically angled or tapered toward the fluid channel so that a width of the contact surface is narrowest adjacent the fluid channel. The contact surface may have an hourglass or bowtie configuration that is configured to funnel the fluid toward the fluid channel to aggregate the fluid within the fluid channel. The contact member typically has a top end and a bottom end that are positioned on opposite ends of the two side edges and the top end commonly has a greater width than the bottom end. The distal end of the treatment fiber is typically centered within the fluid channel so that the distal end of the treatment fiber is fully wettable by the fluid aggregated within the fluid channel. The fluid channel typically has an axial depth from the contact surface of between 3 µm and 300 µm.

In some embodiments, the method may additionally include delivering the treatment light energy through an angle cut of the distal end of the treatment fiber. The treatment light energy may be delivered through the angle cut to bend the treatment light energy away from an axis of the treatment fiber and toward the eye. In some embodiments, the method may additionally include delivering the treatment light energy through a fiber taper element that is coupled with the distal end of the treatment fiber. The treatment light energy may be delivered through the fiber taper element to reduce a divergence angle of a light beam that is emitted from the treatment fiber. The fiber taper element may have a larger egress diameter than an ingress diameter. The fiber taper element may have a conical frustum shape. The ingress diameter may be between about 50 and 100 µm and the egress diameter may be between about 600 and 1000 µm.

BRIEF DESCRIPTION OF THE DRAWINGS

The present embodiments are described in conjunction with the appended figures.

In the appended figures, similar components and/or features may have the same numerical reference label. Further, various components of the same type may be distinguished by following the reference label by a letter that distinguishes among the similar components and/or features. If only the first numerical reference label is used in the specification, the description is applicable to any one of the similar components and/or features having the same first numerical reference label irrespective of the letter suffix.

DETAILED DESCRIPTION

The ensuing description provides exemplary embodiments only, and is not intended to limit the scope, applicability or configuration of the disclosure. Rather, the ensuing description of the exemplary embodiments will provide those skilled in the art with an enabling description for implementing one or more exemplary embodiments, it being understood that various changes may be made in the function and arrangement of elements without departing from the spirit and scope of the invention as set forth in the appended claims.

The embodiments described herein provide improved probes that are configured to treat the eye for various purposes, including the treatment of Glaucoma. According to one aspect, the treatment probes may have a distal tip or end (also referred to herein as a contact member) that enables the treatment probe to move laterally about the eye without lacerating the conjunctival surface of the eye. The improved treatment probes provide increased comfort to the patient that is receiving the treatment procedure. The contact member of the treatment probe includes a contact surface that contacts the eye and that moves laterally about the eye. The contact surface is commonly concave so that the contact surface corresponds to a shape of the eye. The contact surface includes a fluidic channel within which fluid that is present on the surface of the eye is collected or aggregated. The fluidic channel may be a slot or channel that is etched or otherwise formed in the contact surface of the contact member.

The fluid is collected or aggregated in the fluidic channel via edges of the contact member that direct or funnel the fluid toward the fluidic channel as the contact member is moved laterally across the surface of the eye. The edges of the contact member are typically tapered toward the fluidic channel so that fluid that accumulates adjacent the edge is directed or guided toward the fluidic channel. A distal end of a treatment fiber that is disposed within the treatment probe is commonly aligned with a center of the fluidic channel, which allows a physician that is administering the therapeutic treatment to infer a location of a laser treatment spot that will be delivered to tissue of the eye to therapeutically treat the tissue.

In many embodiments, the contact member includes an upper edge that is positioned on one side of the fluidic channel and a lower edge that is positioned on the opposite side of the fluidic channel so that the fluid is directed or guided toward the fluidic channel on both sides of the channel. In a specific embodiment, the edges may have an hourglass or bowtie shape with the fluidic channel in the center of the hourglass or bowtie. The hourglass or bowtie shaped edges funnel the fluid toward the fluidic channel as the contact member is moved laterally across the surface of the eye. The center of the hourglass or bowtie fluidic channel commonly aligns with a center of the treatment fiber that is disposed within the treatment probe. This alignment allows a treating physician to infer the location of the optical treatment spot that will be delivered to the eye to therapeutically treat the eye.

Once the fluid is collected or aggregated in the fluidic channel, the fluid typically will remain within the fluid channel regardless of whether the contact member is moving across the surface of the eye or is positioned stationary relative to the eye. The collected fluid may be fluid that is produced by the eye (i.e., tear film), irrigation or lubricating fluid that is applied to the eye, or commonly a combination of both the natural tear fluid and the irrigation/lubricating fluid.

The collected or aggregated fluid within the fluidic channel is able to contact the distal end of the optical or treatment fiber, which is commonly positioned axially away, from the surface of the eye. The collected or aggregated fluid ideally surrounds the entire distal end of the treatment fiber so that the treatment beam is emitted into the collected or aggregated fluid and is transmitted through the fluid to the eye. The collected or aggregated fluid (e.g., natural tear film and/or irrigation/lubricating fluid) has a refractive index that closely matches the refractive index of the conjunctival surface (mostly water) and surface of the eye. The collected or aggregated fluid may have a refractive index of approximately 1.33-1.34. Thus, when the treatment fiber end face is surrounded by the collected or aggregated fluid (refractive index matching), the treatment beam experiences minimal refraction and reflection between the treatment fiber and the target tissue, thereby ensuring that a greater amount of the treatment energy is delivered to the target tissue and not to non-targeted tissue. In this manner, the collected or aggregated fluid functions as a waveguide for all of the emitted treatment light. A thickness or film of the fluid on the surface of the eye may be roughly 3 μm thick.

Positioning the distal end of the treatment fiber away from the surface of the eye minimizes or eliminates scratching or other damage to the eye from the treatment fiber. The fluid may provide a layer of film between the contact member and the surface of the eye, thereby lubricating the contact member and further reducing or eliminating scratching or other damage to the eye.

According to another aspect, the treatment probes may employ a fiber taper optical element in order to reduce the numerical aperture of the treatment beam. Stated differently the fiber taper optical element may reduce a divergence of the treatment beam that is emitted from the treatment fiber. The fiber taper optical element typically has a small ingress diameter and a larger egress diameter and may reduce the divergence of the treatment beam by expanding a size of the treatment beam. The fiber taper optical element collimates the treatment beam as is exits the distal end of the optical element, which ensures that the treatment spot is focused on the target tissue (e.g. ciliary body, trabecular meshwork, etc.) that is positioned posterior to the surface of the eye. This helps ensure that an increased photon density of light energy, or stated differently an increased amount of light energy, is delivered to the target tissue rather than being scattered and deflected within the eye and being incident on non-targeted tissue within the eye. If the treatment beam is too divergent, then the photon flux passing through the treatment spot may be too low to deliver the therapeutic treatment desired. This problem may be especially pertinent when short duration pulses of the treatment light are emitted in a manner that therapeutically treats the eye. In such instances, it is increasingly important to ensure that most or a substantial majority of the treatment energy is delivered to the target tissue.

The fiber taper optical element is typically a component that is separate from the optical or treatment fiber and that is attached to the distal end of the treatment fiber. However, in some embodiments, the fiber taper optical element may be formed on the distal end of the treatment fiber or formed as part of the contact member. The fiber taper optical element is typically disposed within the contact member so that when the contact member is coupled with the distal end of the treatment probe, the fiber taper optical element is axially aligned with the treatment fiber.

Having described various embodiments generally, additional aspects and features of the invention will be more readily apparent with reference to the description of the various figures provided herein below.

Figure 1A:
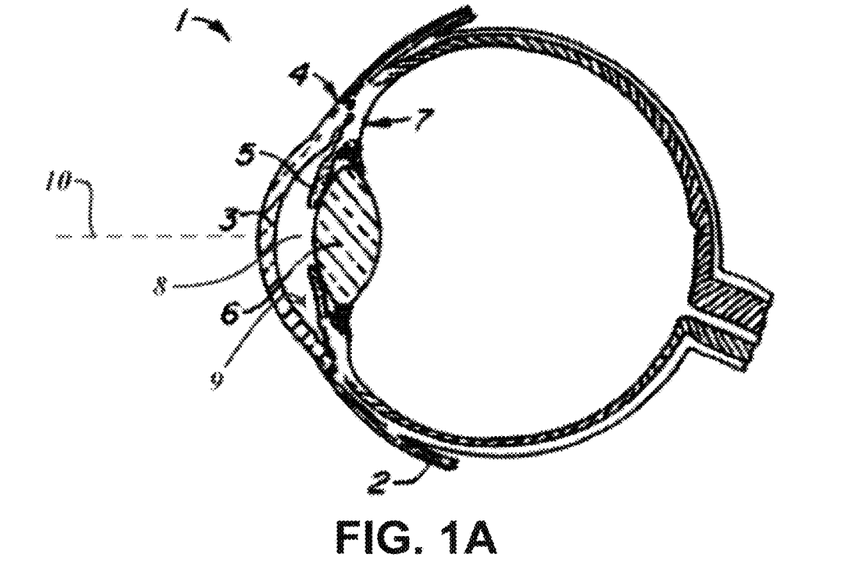
FIG. 1A illustrates the anatomy of an eye with relevant parts labeled to provide anatomical references.

FIG. 1A illustrates the anatomy of an eye 1 with relevant parts labeled to provide anatomical references. The sclera 2 is a tough sheath around the eye which meets the cornea 3 at a circular junction called the limbus 4. Behind the cornea 3 lies the iris 5, the lens 6 and the ciliary body and related processes 7. The anterior chamber is the fluid-filled compartment within the eye 1 just in front of the pupil 8. Viewed in profile, the anterior chamber is bounded by the domed cornea 3 in front and by the colored iris 5 behind. Where the cornea 3 and the iris 5 converge they form an angle 9 referred to herein as the angle of the anterior chamber. Further eye 1 may have a visual/optical axis 10.

Figure 1B:
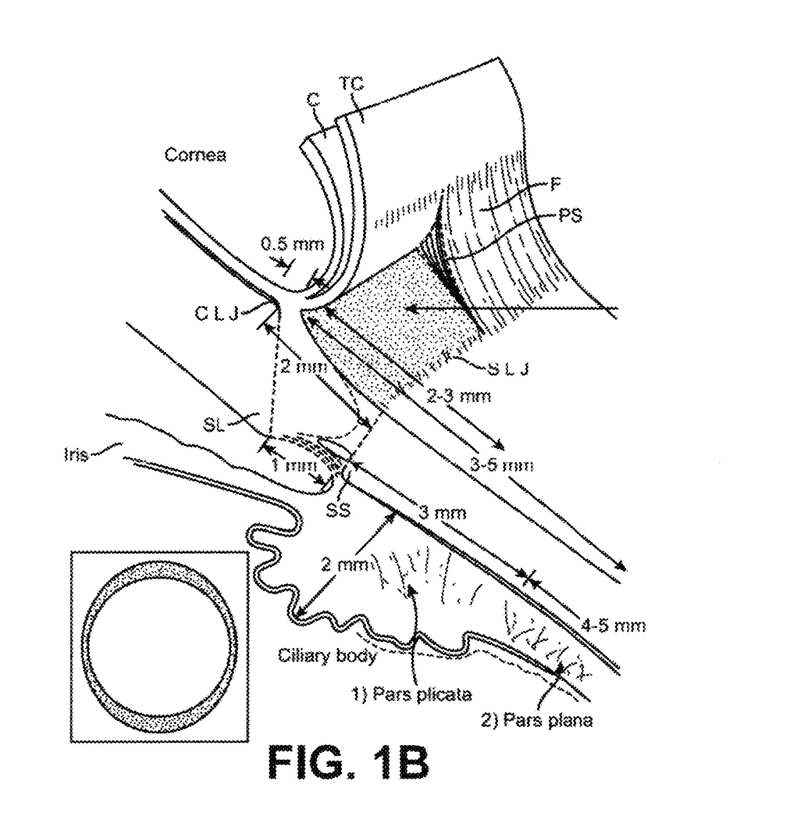
FIG. 1B illustrates further details of the surgical eye anatomy.

FIG. 1B illustrates further details of the surgical eye anatomy. Embodiments described herein may target intraocular structures (also referred to herein as target tissue) that span from the posterior pars plicata to the pars plana. Alternatively, the pars plana may be targeted and the pars plicata, ciliary body, and other ciliary processes avoided.

Figure 2A:
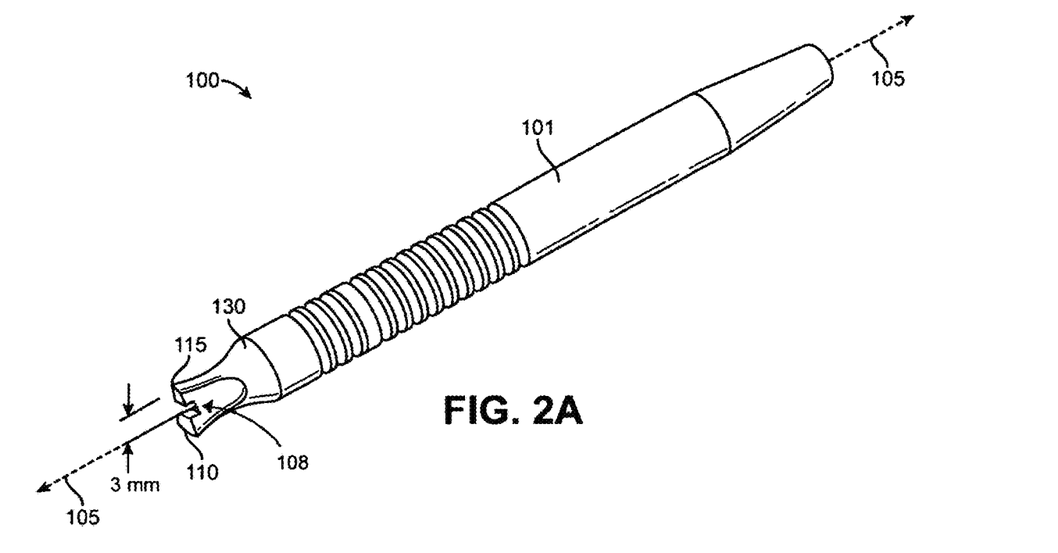
FIG. 2A illustrates an exemplary embodiment of a treatment probe.

FIG. 2A illustrates a treatment probe 100 according to one embodiment. Treatment probe 100 comprises an elongate body 101 and a contact member 130 disposed on one end of the elongate body 101. The elongate body 101 defines a handle that may be grasped by a physician to control the treatment probe during the therapeutic treatment. The elongate body 101 has a proximal end and a distal end and defines a treatment axis 105. In some embodiments, the treatment probe 100 has an input end, an output end, a top, a bottom and sides. The elongated body 101 is adapted to receive a fiber optic or treatment fiber 120 that is configured to deliver a treatment beam (e.g., laser or light beam) to a patient's eye E. The treatment fiber 120 is housed within the elongate body 101 and is configured to deliver treatment light energy to the patient's eye E from a distal end of the treatment fiber 120. The eye E has a shaped sclera, a limbus and an optical axis 200. The contact member 130 of the treatment probe 100 defines a contact surface 110 that conforms to the shape of the sclera at the limbus when the axis 105 of the treatment probe forms a predetermined angle relative to the optical axis 200 of the eye E.

In particular, the contact surface 110 conforms to the shape of the sclera at the limbus when the axis of the treatment probe 100 is substantially perpendicular to the conjunctiva-sclera point of indentation of the eye E. The conforming shape of the contact surface 110 enables the contact member 130 to be positioned on the surface of the eye E and easily moved about the surface of the eye E. The conforming shape of the contact surface 110 also facilitates in the contact member collecting or aggregating fluid within a fluid or fluidic channel 108 that is formed on or within the contract surface 110. Specifically, the conforming shape of the contact surface 110 allows the edges, 132 and 134, of the contact member 130 to contact fluid on the surface of the eye E when the contact member 130 is moved laterally across the surface of the eye E. The edges, 132 and 134, are shaped to direct or funnel the fluid toward the fluid channel 108 as the contact member 130 is moved laterally across the surface of the eye E. The fluid channel 108 is shaped so that the fluid collects or aggregates within the fluid channel 108 and contacts the distal end of the treatment fiber 120.

The treatment probe 100 is specifically designed for the efficient transconjunctival/transscleral delivery of light energy to the target tissue. The light energy may be delivered over the posterior region of the pars plicata, over the pars plana—pars plicata junction, and the like. The laser energy preferably has excellent scleral transmission characteristics. The laser energy may be provided from an infrared diode laser energy source, such as a pulsed laser having a wavelength of 810 nm. In other instances, the wavelength of laser energy may be 514 nm, 532 nm, 577 nm, 910 nm, 1064 nm, or any other laser wavelength and power that is effective for glaucoma treatment. Optical energy from other sources, for example, light emitting diodes (LEDs), may be delivered as well.

The contact surface 110 is designed to ensure that the light energy is directed substantially perpendicular to the conjunctiva/sclera point of indentation. As described in greater detail herein, the contact surface 110 is designed to allow the physician to administer the treatment either with a continuously 360° sliding motion over the conjunctiva overlying the pars plana or, with a series of individual applications with defined angular spacing or radial displacements. The contact surface 110 may have a single radius of curvature across the contact surface 110 and no sharp edges.

In some embodiments, the contact member 130 includes a limbal placement edge 115, which may be positioned on a short side of the contact surface 110. The limbal placement edge 115 has a contact surface contour that conforms to the limbus and is generally circularly concave with a radius of about 5.25-6.0 mm. The treatment fiber 120 is typically positioned a distance of between 1.5-4.0 mm from the limbal placement edge 115 to facilitate the optimal irradiation over the eye's pars plana—pars plicata junction and/or over the eye's pars plana. In a specific embodiment, the treatment fiber 120 is positioned a distance of between 2.0 or 3.0 mm from the limbal placement edge 115.

The treatment fiber 120 may be coupled with a console (not shown) that is configured to generate the treatment light for treating the patient's eye. The console may, for example, generate a 810 nm infrared treatment laser. Additionally, in some embodiments, the console may be configured to generate illumination light (e.g., white light) for illuminating various parts of the eye. The console may include one or more outlets for outputting the treatment light and/or illumination light and may be configured to couple with the treatment fiber 120 by receiving a proximal connection end of the treatment fiber 120. Once coupled to the console, the treatment fiber 120 may deliver the treatment light and/or illumination light from the console to a distal end of the treatment probe 100 via optical waveguides, fiber optics, light conduits, light guides, light tubes, or the like.

Figure 2B:
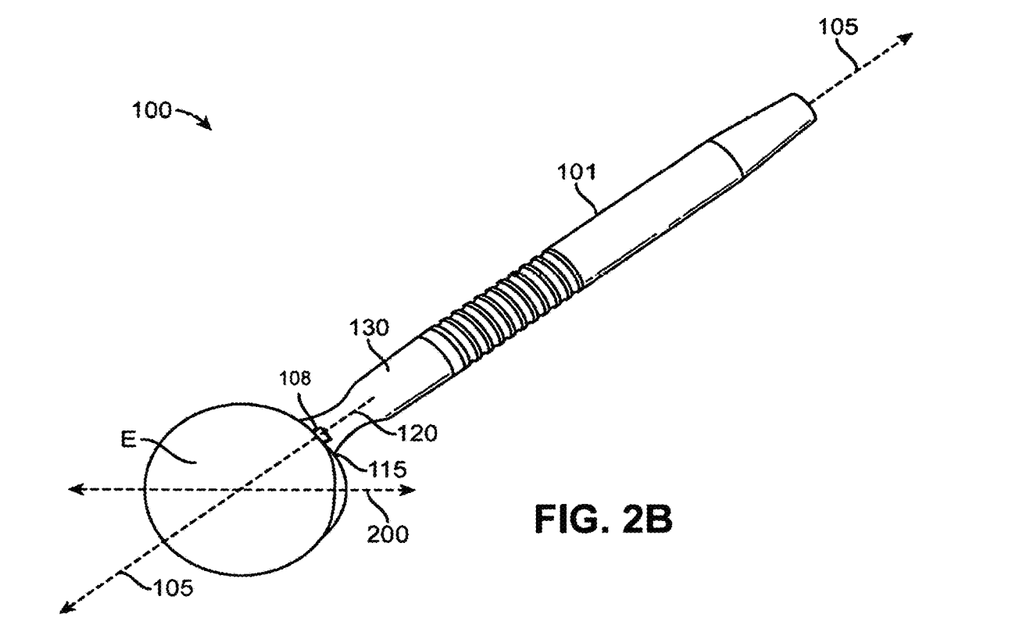
FIG. 2B illustrates the treatment probe of FIG. 2A positioned against the eye.

FIG. 2B illustrates the treatment probe 100 positioned against the eye E with the short limbal placement edge 115 next to the limbus. FIG. 2B further illustrates the treatment probe 100 directing light energy radially to the eyeball center over the pars plana—pars plicata junction, generally indicated by the axis 105. Alternatively, the treatment probe 100 may direct light energy radially over any other structure posterior the limbus, such as the ciliary body.

Figure 3A:
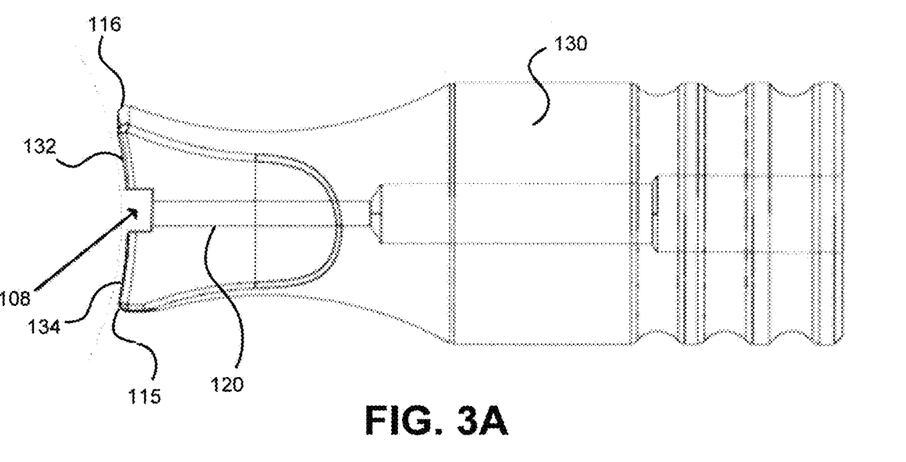
FIGS. 3A-C illustrate a contact member of the treatment probe of FIG. 2A in greater detail.
Figures 3B, 3C:
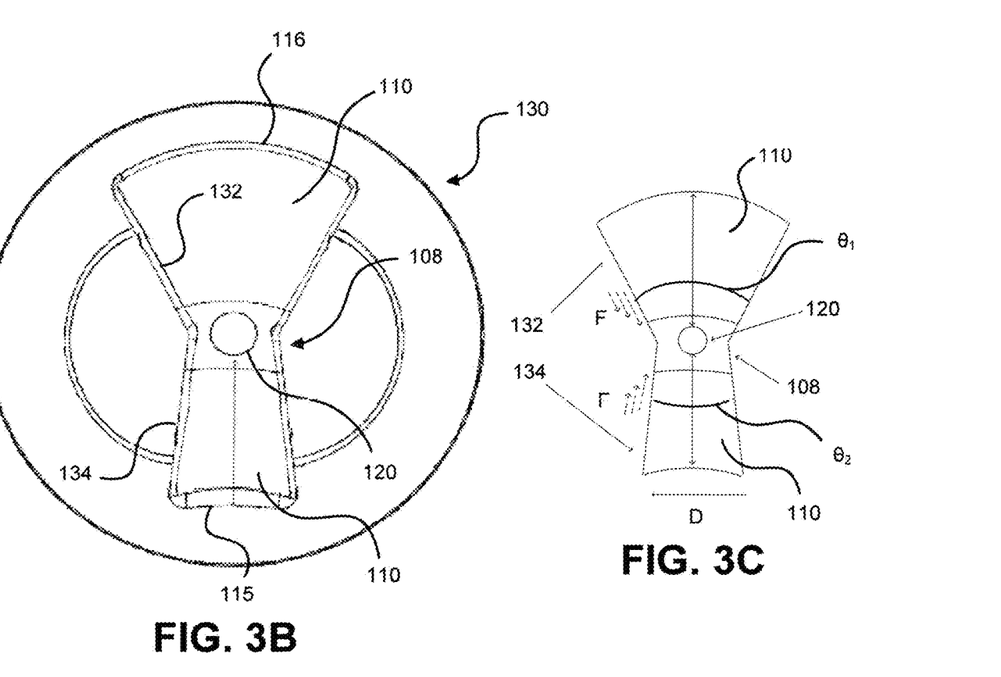

FIGS. 3A-C illustrate the contact member 130 in greater detail. The contact member 130 may be fixedly secured to the distal end of the treatment probe 100 or may be a removable and replaceable component of the treatment probe 100. FIG. 3A is side view of the contact member 130 and FIG. 3B is a front view of the contact member 130. FIG. 3C illustrates the contact surface 110 of the contact member 130 in isolation from the remainder of the contact member 130. As illustrated in FIG. 3A, the contact member 130 is shown positioned atop the eye E. The contact surface 110 has a shape that correspond to the surface of the eye E, and more specifically the shape of the sclera. Specifically, the contact surface 110 is concave and has a shape that is approximately the inverse of the curvature of the eye E or sclera. The treatment fiber 120 is shown disposed within the interior of the contact member 130. The fluid channel 108 is also clearly illustrated in relation to the eye E. The fluid channel 108 may be formed via a slot or channel that is etched or otherwise formed in the distal end of the contact member 130 and in the contact surface 110. The fluid channel 108 is positioned roughly centrally about the contact member 130 between an upper tapered end and a lower tapered end of the contact surface 110. The upper tapered end includes an upper side edge 132 and the lower tapered end includes a lower side edge 134. The upper side edge 132 and the lower side edge 134 are both tapered or angled toward the fluid channel 108 so that a width of the contact surface 110 is narrowest adjacent to the fluid channel 108 or adjacent to the fluid channel's inlet. As illustrated in FIG. 3B, the upper tapered end and the lower tapered end are commonly mirrored about a plane that passes through the contact member 130 perpendicular to the contact surface 110. The upper tapered end may have an angle $\theta_1$ of between 30 and 60 degrees and the lower tapered end may have an angle $\theta_2$ of between 15 and 45 degrees. In some embodiments, such as the embodiment illustrated in FIG. 3B, angle $\theta_1$ is different than angle $\theta_2$. In FIG. 3B, angle $\theta_1$ is greater than angle $\theta_2$. In other embodiments, angle $\theta_1$ may be the same as angle $\theta_2$.

The upper side edge 132 and the lower side edge 134 are configured or shaped to direct fluid F toward the fluid channel 108 when the contact member 130 is moved in a lateral direction D across the surface of the eye. When the contact surface 110 has an hourglass or bowtie configuration, the contact surface 110 may also direct fluid F toward the fluid channel 108 when the contact member 130 is moved in a lateral direction that is opposite to direction D. The fluid F flows toward and into the fluid channel 108 and is collected or aggregated within the fluid channel 108 as the contact member 130 is moved laterally across the eye's surface. The fluid F may be the natural tear fluid of the eye or may be an irrigating or lubricating fluid that is applied to the surface of the eye. In many embodiments, the fluid F is a combination of both the natural fluid and an irrigating fluid.

In the embodiment illustrated in FIGS. 3B and 3C, the contact surface 110 has an hourglass or bowtie configuration that is configured to funnel, direct, or guide the fluid F toward the fluid channel 108 in order to aggregate the fluid within the fluid channel 108. In some embodiments an upper edge 116 of the contact surface 110 may have a greater width than the placement edge 115. In other embodiments, the width of the upper edge 116 and the placement edge 115 may be approximately the same.

The distal end of the treatment fiber 120 is typically centered within the fluid channel 108. The treatment fiber 120 may be separated from the placement edge 115 by at least 1.5 mm, and more commonly 3 mm or 4 mm depending on an individual patient's anatomy. The treatment fiber 120 may also be separated from the upper edge 116 by at least 1.5 mm and sometimes 3 mm. Centering of the treatment fiber 120 within the fluid channel 108 allows a physician to infer the location of a treatment beam spot that will be delivered to the target tissue from the treatment fiber 120.

A diameter of the treatment fiber's distal end is typically smaller than a width of the fluid channel 108. The smaller diameter treatment fiber 120 enables the fluid F that is aggregated or collected within the fluid channel 108 to entirely surround the distal end of the treatment fiber 120. Since the fluid F has a refractive index that substantially matches that of the eye E, the fluid F is able to function as a waveguide for the emitted light and thereby ensure that substantially all of the treatment light energy is delivered to the target tissue. When an irrigating or lubricating fluid is applied to the surface of the eye, the refractive index of the irrigating or lubricating fluid should match the refractive index of the eye.

The fluid channel 108 has a width that is greater than a diameter of a distal end of the treatment fiber and is commonly between 400 μm and 1000 μm. For example, if the diameter of treatment fiber's distal end is 600 μm, the width of the fluid channel 108 could be anything larger than 600 μm, such as 1000 μm. The fluid channel 108 is also configured to span the contact member 130, or stated differently extend from opposing sides of the contact member 130, as illustrated in FIGS. 3B and 3C in order to allow fluid to flow into the recessed area from either side of the contact member 130. The fluid channel 108 may also have an axial depth from the contact surface 110 of between 3 μm and 300 μm. In a specific embodiment, the fluid channel may have an axial depth of between about 50 μm and 100 μm. The fluid channel 108 is configured to collect or aggregate the fluid F whether the treatment probe 100 is moving or stationary. The distal tip of the treatment fiber 120 is typically positioned axially away from the surface of the eye and from the contact surface 110. The distal end of the treatment fiber 120 may be flush with the fluid channel or may extend distally of a back wall of the fluid channel 108. The distal end of the treatment fiber 120 may be a flat polished tip or ball tipped fiber as desired. Regardless of the fiber tip that is employed, the aggregated or collected fluid F contacts the distal end to provide the refractive index matching advantages described herein.

Figure 4A:
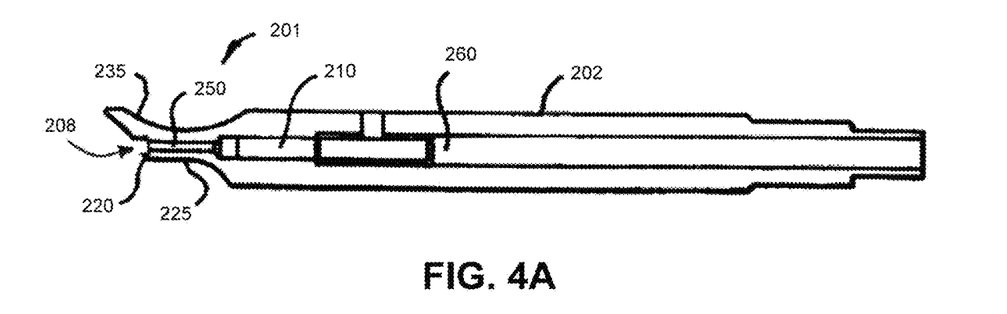
FIG. 4A illustrates another exemplary embodiment of a treatment probe.
Figure 4B:
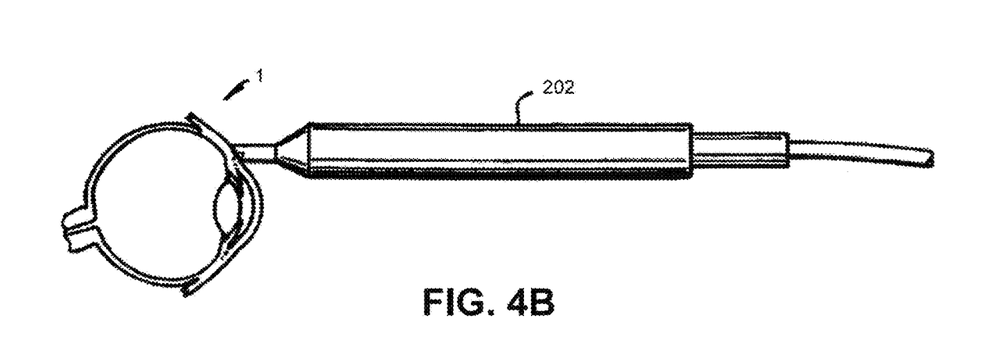
FIG. 4B illustrates the treatment probe of FIG. 4A positioned against an eye.

FIG. 4A illustrates another embodiment of a treatment probe 202 and FIG. 4B illustrates the treatment probe 202 positioned against an eye 1. The contact member 201 of the treatment probe 202 has a contact surface 212 that is shaped or contoured to correspond to a shape of the eye 1. Specifically, a curvature of the contact surface 212 essentially matches a curvature of the eye, which enables the contact surface 212 to be positioned essentially flush against the eye 1. The contact surface 212 also has a reference edge 220 that is positionable against a feature of the eye 1, such as the limbus to align the treatment probe 202 in a proper orientation for delivery of the treatment light energy. As shown in FIG. 4B, the treatment probe 202 may be aligned so that the treatment light energy (e.g., laser energy) is delivered parallel to the eye's optic axis.

FIG. 4A is a side view of the treatment probe 202. As illustrated in FIG. 4A, the contact surface 212 includes an opening 210 for the treatment fiber 200. As briefly mentioned above, the contact surface 212 is contoured to conform to the shape of the eye, particularly when the axis of the treatment probe 202 is parallel to the optic axis of the eye 1. The shape of the contact surface 212 can be closely approximated as a concave spherical section of radius 5.5 mm to 6.0 mm with the spherical center being located about 6.7 mm to 6.9 mm below the opening for the treatment fiber 200.

Along the bottom of the contact surface 212 is the reference edge 220 with a placement contour 225 extending away from the reference edge 220 toward a main body of the treatment probe 202. The reference edge 220 is shaped to conform to the limbus of the eye 1. Particularly, the reference edge 220 is concave with a radius of about 5.5-6.0 mm and is positioned about 1.2 mm from the opening 210 at its closest approach. The reference edge 220 may be used to facilitate optimal alignment of the treatment fiber 200 with the eye's ciliary body. The contact member 201 also includes an eyelid lifting contour 235, which is a circular concavity in an upper surface of the contact member 201. The eyelid lifting contour 235 may have a radius about 25 mm and a center of curvature located about 31 mm above the axis of the treatment probe 202.

The placement contour 225 is shown extending away from reference edge 220 and the treatment fiber 200 is shown within a narrow bore 250 that extends slightly out from the contact surface 212. The output tip of treatment fiber 200 is normally polished flat, but may have a ball tipped configuration as desired. The treatment fiber 200 is also illustrated within a wide bore 260 of the treatment probe 202. The fluid channel 208 is illustrated in FIG. 4A. As previously described, the fluid channel 208 is a slot of channel that is etched, cut, or otherwise formed in the contact surface 212 of the contact member 201. The distal end of the treatment fiber 200 is disposed within the fluid channel 208 and is often flush with a rear surface of the fluid channel 208, although in some embodiments the distal end of the treatment fiber 200 may extend into the fluid channel 208 by some amount, such as when the distal end has a ball tipped configuration.

Figure 5A:
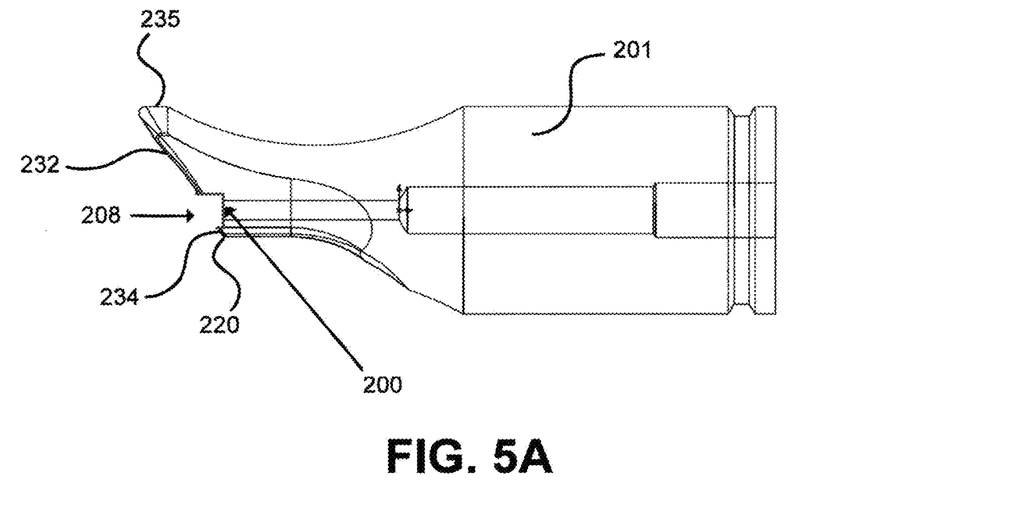
FIGS. 5A-B illustrate a contact member of the treatment probe of FIG. 4A in greater detail.
Figure 5B:
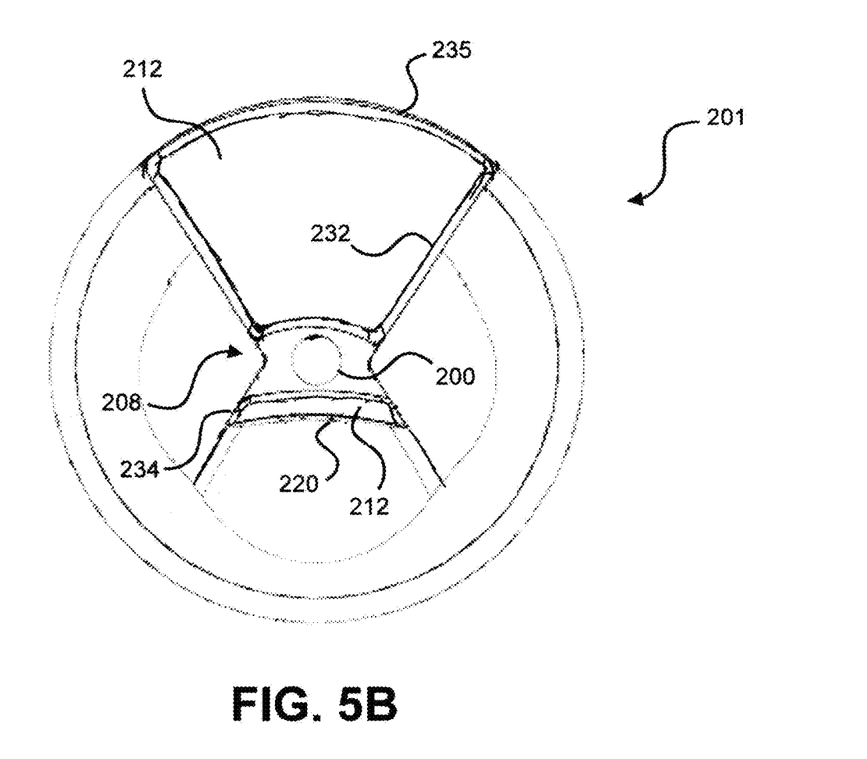

The fluid channel 208 and the contact member 201 are illustrated in greater detail in FIGS. 5A-B. The contact member 201 may be fixedly secured to the distal end of the treatment probe 202 or may be a removable and replaceable component of the treatment probe 202. The treatment fiber 200 is shown disposed within the interior of the contact member 201. The fluid channel 208 is positioned roughly centrally about the contact member 201 between an upper tapered end and a lower tapered end of the contact surface 212. The upper tapered end includes an upper side edge 232 and the lower tapered end includes a lower side edge 234. The upper side edge 232 and the lower side edge 234 are both tapered or angled toward the fluid channel 208 so that a width of the contact surface 212 is narrowest adjacent to the fluid channel 208 or adjacent to the fluid channel's inlet. A radial width of the lower tapered end is substantially thinner than a radial width of the upper tapered end, which allows the reference edge 220 to be positioned adjacent the limbus with the axis of the treatment probe 202 aligned with the optical axis of the eye 1.

The upper side edge 232 and the lower side edge 234 are configured or shaped to direct fluid toward the fluid channel 208 when the contact member 201 is moved in a laterally direction across the surface of the eye. The fluid flows toward and into the fluid channel 208 and is collected or aggregated within the fluid channel 208 as the contact member 201 is moved laterally across the eye's surface. The fluid may be the natural tear fluid of the eye, may be an irrigating or lubricating fluid that is applied to the surface of the eye, or may be a combination of both the natural fluid and the irrigating fluid. Although the lower tapered end is substantially thinner radially than the upper tapered end, the contact surface 212 typically has an hourglass or bowtie configuration that funnels, directs, or guides the fluid toward the fluid channel 208 in order to aggregate or collect the fluid within the fluid channel 208.

The distal end of the treatment fiber 200 is typically centered within the fluid channel 208. The treatment fiber 200 is separated from the reference edge 220 by less than 2 mm. Centering of the treatment fiber 200 within the fluid channel 208 allows a physician to infer the location of a treatment beam spot that will be delivered to the target tissue from the treatment fiber 200. A diameter of the treatment fiber's distal end is typically smaller than a width of the fluid channel 208, which enables the fluid that is aggregated or collected within the fluid channel 208 to entirely surround the distal end of the treatment fiber 200. Thus, like the embodiment of FIGS. 3A-4B, the treatment probe 202 benefits from the refractive index matching of the aggregated/collected fluid and the eye, which results in a substantial increase in the delivery of the treatment light energy to the target tissue.

The fluid channel 208 may have a width that is greater than a diameter of the distal end of the treatment fiber as previously described. The fluid channel 208 may also have an axial depth from the contact surface 212 of between 3 μm and 300 μm. In a specific embodiment, the fluid channel may have an axial depth of between about 50 μm and 100 μm. The fluid channel 208 is capable of aggregating the fluid regardless of whether the treatment probe 202 is moved or is held stationary.

Figure 6A:
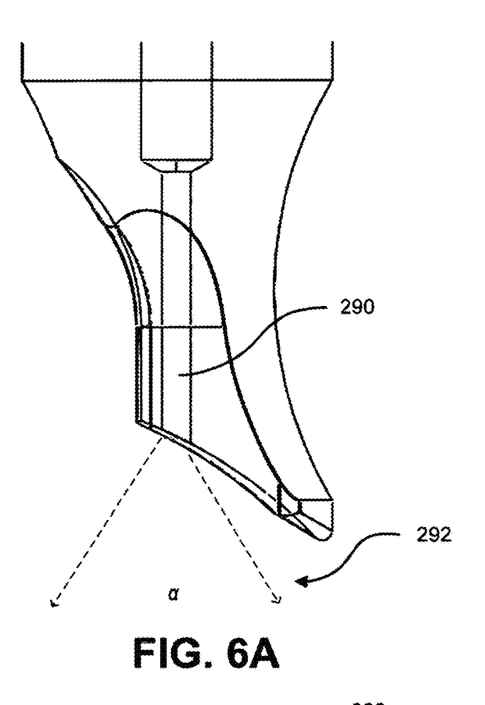
FIG. 6A illustrates a straight fiber tip that may be employed with the contact members of FIGS. 3A-C and/or FIGS. 5A-B.
Figure 6B:
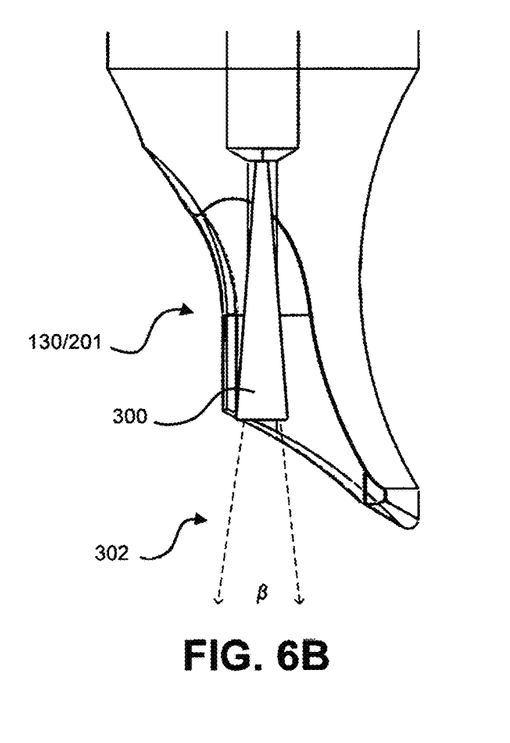
FIGS. 6B-C illustrate a fiber taper optical element that may be employed with the contact members of FIGS. 3A-C and/or FIGS. 5A-B.
Figure 6C:
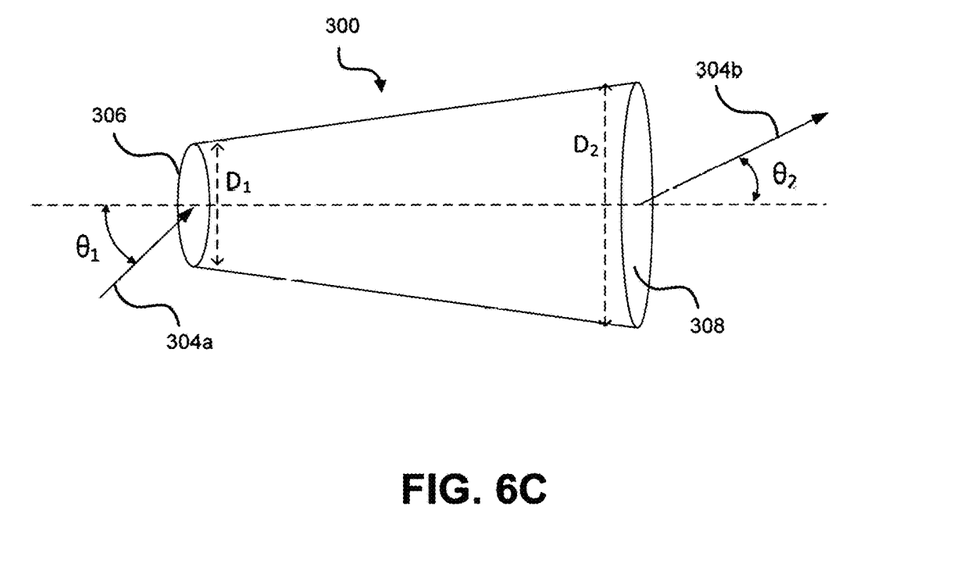

FIGS. 6B-C illustrate a fiber taper optical element that may be employed with the contact members described herein—i.e., employed with the contact member 130 or the contact member 201. The fiber taper optical element is used to reduce a numerical aperture of the treatment beam that is emitted from the respective treatment fiber 120/200. Stated differently, the fiber taper optical element is used to reduce a divergence of the treatment beam that is emitted from the treatment fiber 120/200. FIG. 6C illustrate an exemplary fiber taper optical element 300 in isolation while FIG. 6B illustrates the fiber taper optical element 300 (hereinafter fiber taper 300) positioned within a contact member 130/201. As illustrated in FIG. 6C, the fiber taper 300 has a proximal end 306 and a distal end 308. The fiber taper 300 has a generally conical frustum shape in which an egress diameter $D_2$ is larger than an ingress diameter $D_1$. The conically frustum shaped fiber taper 300 reduces a divergence angle of an optical beam that is emitted from the treatment fiber 120/200. For example, a treatment beam 304a that is transmitted to the proximal end 306 of the fiber taper 300 may have a divergence angle of $\theta_1$ and the fiber taper 300 may reduce the divergence angle so that a treatment beam 304b emitted from the distal end 308 of the fiber taper has a divergence angle of $\theta_2$ that is less than the divergence angle $\theta_1$. In this manner, the fiber taper 300 collimates the treatment beam that is emitted from the treatment fiber 120/200, which ensures that a resulting treatment spot is increasingly focused on the targeted tissue (e.g. ciliary body, trabecular meshwork, etc.) positioned posterior to the surface of the eye.

The approximate relationship between the input beam angle $\theta_1$, the ingress diameter $D_1$, the egress diameter $D_2$, and the output beam angle $\theta_2$ may be represented by the equation $D_1 \sin \theta_1 = D_2 \sin \theta_2$. From this equation it is evident that with an ingress diameter $D_1$ of 100 μm and an egress diameter $D_2$ of 600 μm, the numerical aperture of the treatment beam could be reduced by a factor of 6, which would greatly reduce the spot size on the target tissue to be therapeutically treated with the treatment beam. In some embodiments, the ingress diameter $D_1$ may be between about 50 and 100 μm and the egress diameter $D_2$ may be between about 600 and 1000 μm. The fiber taper 300 may have a longitudinal length of between 1 mm and 10 mm.

FIG. 6B illustrates the fiber taper 300 coupled with the contact member 130/201 and optically coupled with the distal end of the treatment fiber 120/200. FIG. 6A illustrates a straight fiber tip 290 employed with the contact member 130/201. A comparison of FIGS. 6A and 6B demonstrates a reduction in the divergence angle of the emitted treatment beam. Specifically, FIG. 6A illustrates a treatment beam 292 that diverges from the distal end of the straight fiber tip 290 at an angle α while FIG. 6B illustrates a treatment beam 302 that diverges from the distal end of the fiber taper 300 at an angle β, which is substantially reduced in comparison with angle α. The reduction in the divergence angle represented by angle β results in an increased the photon density of light energy that is transmitted to the targeted tissue. The increase photon density of light energy results in an increased amount of light energy being able to therapeutically treat the targeted tissue rather than being scattered within the eye and absorbed or reflected by non-targeted tissue. The increased photon density may be especially important when the therapeutic treatment involves a series of short duration low energy pulses as described herein since ensuring a therapeutic response to each pulse is highly desired to ensure that a prescribed treatment is provided.

In addition, the use of the fiber taper 300 may allow a lower cost treatment fiber 120/200 to be used without negatively impacting the resulting therapeutic treatment. For example, if an egress spot size of 600 μm is desired for the treatment beam, a 50 μm or 100 diameter multimode treatment fiber may be used with a 100 μm or 600 μm fiber taper 300 coupled with the distal end of the treatment fiber. The fiber taper 300 would enlarge the spot size to approximately 600 μm while greatly reducing the divergence angle of the treatment beam, thus ensuring that the desired spot size is delivered to the targeted tissue with an substantially increased photon density of treatment light. In many applications a large treatment beam spot size may be preferred, which could be easily provided with the fiber taper 300.

A distal surface of the fiber taper 300 may be flat polished to further realize the collimation effect without expensive techniques such as forming a ball shaped tip with heat. The flat polished fiber taper end may minimize the risks of scratching the eye. In other embodiments, however, a ball shaped tip may be formed in the fiber taper end if desired. The fiber taper 300 is typically a separate component from the treatment fiber 120/200 and contact member 130/201. The contact member 130/201 may have a tapered channel to accommodate the fiber taper 300 and the fiber taper 300 may be permanently or removably coupled with the contact member 130/201. In other embodiments, the fiber taper 300 may be a component that is integrally formed or coupled with the contact member 130/201 or the fiber taper 300 may be formed in the distal end of the treatment fiber 120/200. The fiber taper 300 may be used with a contact member having a fluid channel 108/208 as described herein, or may be used with a contact member that does not include a fluid channel if desired. However, the use of the fiber taper 300 with the fluid channel typically provides the refractive index matching and waveguide benefits described herein due to the aggregated fluid. Thus, the use of the fiber taper 300 with a fluid channel may be preferred.

Figure 7:
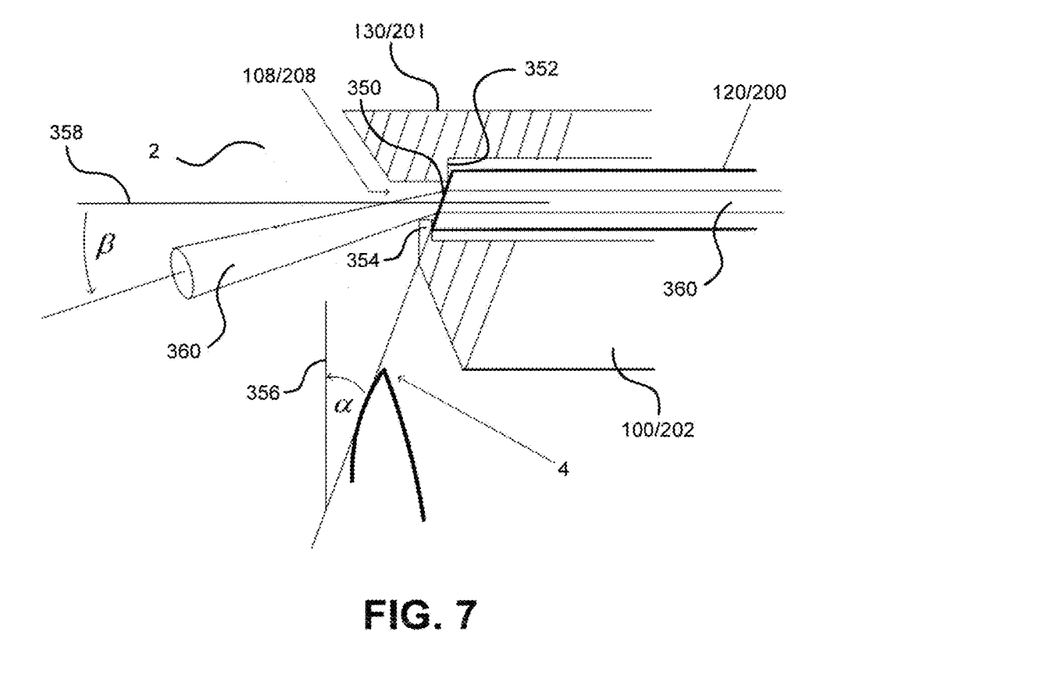
FIG. 7 illustrate a contact member of a treatment probe that is configured to bend a treatment beam as the beam exits a distal end of the treatment probe and contact member.

FIG. 7 illustrates a contact member of a treatment probe that is configured to bend a treatment beam as the beam exits a distal end of the contact member. The contact member bends the treatment beam 360 so that the beam 360 is more normal to the sclera 2 of the eye, which aids in delivering the beam 360 to desired tissue within the eye. The contact member may be the contact member 130/201 of the previously described treatment probes 100/202. To bend the treatment beam 360, a distal end 350 of the treatment fiber 120/200 is cut at angle (i.e., bias cut) relative to a plane 356 that is normal to an axis 358 of the treatment fiber 120/200. The distal end 350 of the treatment fiber 120/200 is cut at angle α relative to the plane 356. The angle α may be between 10 and 80 degrees, and in some embodiments between 20 and 70 degrees. The treatment fiber 120/200 is cut so that a sharp tip of the treatment fiber's distal end 350 is closer to the limbus 4 of the eye as illustrated in FIG. 7. The distal end of the contact member 130/201 includes two edges, 352 and 354, that contact a face of the angle cut distal end 350 of the treatment fiber 120/200. The edges, 352 and 354, help to prevent the treatment fiber 120/200 from protruding beyond the distal end of the contact member 130/201. In some embodiments, the edges, 352 and 354, may not be included and other means of fixing the treatment fiber 120/200 in position relative to the contact member 130/201 may be employed. The contact member 130/201 includes the fluid channel 108/208 within which fluid is aggregated as previously described. The contact member 130/201 is shaped and configured to direct fluid toward the fluid channel 108/208 as previously described.

The angle cut distal end 350 of the treatment fiber 120/200 directs the treatment beam 360 away from the axis 258 of the treatment fiber 120/200 by an angle β. The angle cut of the treatment fiber's distal end 350 functions to some degree as a prism that aids in bending the treatment beam 360 toward the sclera 2. The bending of the treatment beam 360 is also influenced by the refractive index of the treatment fiber 120/200 and the fluid that is aggregated within the fluid channel 108/208. The angle β may be determined by the equation $\beta=\arcsin[(n_2/n_1)*\sin \alpha]-\alpha$, in which $n_1$ is the refractive index of the treatment fiber 120/200 (e.g., approximately 1.45) and $n_2$ is the refractive index of the aggregated fluid within the fluid channel 108/208, which fluid may be air, irrigation fluid, natural tear/fluid produced by the eye, and the like. The refractive index $n_2$ may be approximately 1.0 for air, 1.33-1.34 for the aggregated fluid, and the like. In the above equation, the relationship between $\beta$ and $\alpha$ is typically known, such as by assuming the angle cut distal end 350 functions similar to a prism on the flat cut treatment fiber. It should be noted that a prism refracts different wavelengths of light at different angles and thus, the relationship of $\beta$, $n_1$, $n_2$, $\alpha$ is only an approximation. In some embodiments, the angle $\beta$ may be between 10 and 50 degrees.

As briefly mentioned above, the angle cut distal end 350 of the treatment fiber 120/200 aids in delivering the beam 360 to desired tissue within the eye. Specifically, bending the treatment beam 360 allows the treatment beam 360 to be directed more perpendicularly relative to the surface of sclera 2, which allows the tissue that is directly underneath the sclera 2 to be irradiated to a greater degree since the treatment light is contacting the tissue at a more perpendicular angle. The angle cut distal end 350 may be particularly useful for an ophthalmic laser treatment where the target area is directly underneath the sclera. In some embodiments, the contact member 130/201 may not include the fluid channel 108/208. In such embodiments, the sharp tip of the treatment fiber's angle cut distal end 350 may be approximately flush with the surface of distal end of the contact member 130/201.

Figure 8A:
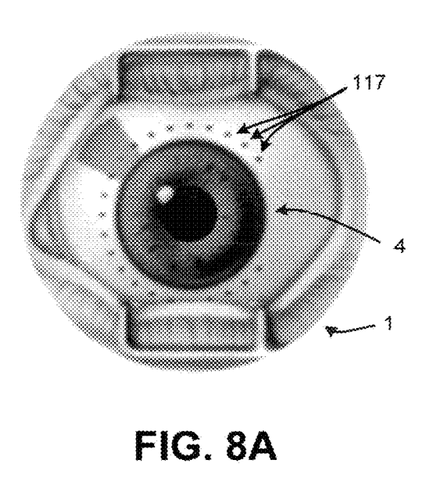
FIGS. 8A-B illustrate treatment procedures that may be employed to treat the eye.
Figure 8B:
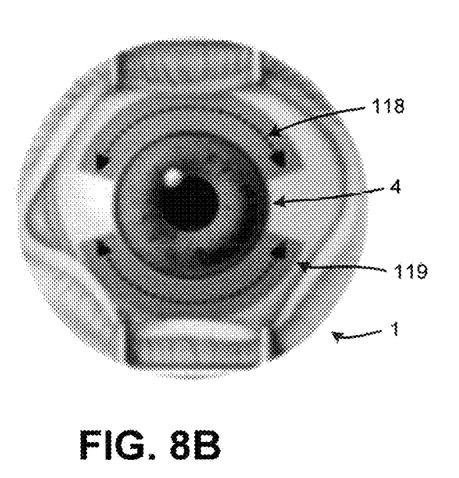

FIGS. 8A-B illustrate treatment procedures that may be employed to treat the eye. FIG. 8A illustrates a treatment procedure that includes a plurality of spaced apart fixed locations 117 about the limbus 4 of the eye. Each of the spaced apart locations are treated with therapeutic light. The treatment of the spaced apart fixed locations 117 is described in U.S. Patent Publication 2010/0076419, which is incorporated herein by reference. In the treatment described in the '419 publication, a laser probe is moved and repositioned about the eye in order to treat each spaced apart fixed location 117 individually. In the embodiment described herein, the treatment probe (e.g., treatment probe 202) could be moved to each fixed location 117 and a treatment beam could be delivered to each fixed location 117. In delivering the treatment, the therapeutic light may be delivered once to each spaced apart fixed location 117, or may be delivered multiple times to each spaced apart fixed location 117 as described below.

FIG. 8B illustrates another treatment method, in which a treatment probe (e.g., treatment probe 100) is slid or swept across target tissue concurrently with the light delivery. The treatment method results in an arcuate or curved pattern of treated tissue, 118 and 119, above and below the limbus 4. This treatment method is described in U.S. Patent Publication 2015/0374539, which is incorporated herein by reference in its entirety. In the embodiment described herein, the treatment probe could be swept across the target tissue while the treatment beam is delivered to the target tissue. In delivering the treatment, the therapeutic light may be delivered once to the arcuate/curved pattern, 118 and 119, or may be delivered multiple times to the arcuate/curved pattern, 118 and 119, as described below.

Figure 9:
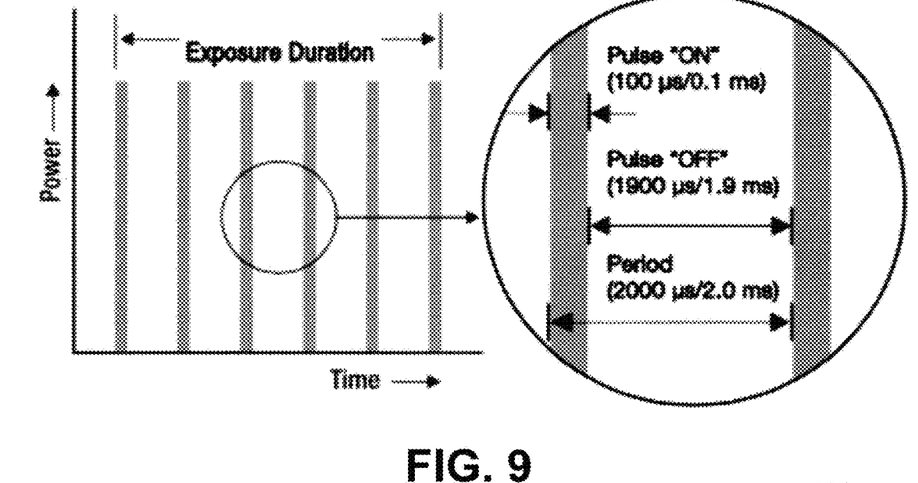
FIG. 9 illustrates an exemplary pulsed mode that may be used to treat tissue of the eye.

The treatment fiber 120/200 may be configured to deliver light energy in a pulsed or continuous wave emission mode. For example, in some embodiments, the light energy may be delivered with a 30% duty cycle having an "on" time of about 500 μs and an "off" time of about 1100 μs. In other embodiments, the light energy may be delivered with a 15% duty cycle having an "on" time of about 300 μs and an "off" time of about 1700 μs, or about a 10% duty cycle having an "on" time of about 200 Us and an "off" time of about 1800 μs. Careful selection of the laser energy pulse "on" and "off" times can avoid undesired thermal damage to a target by allowing the target to cool during the "off" time of the laser before the next pulse of energy is delivered during the "on" time. The duty cycle may be selected so that cumulative thermal buildup, caused by insufficient cooling during the "off" time may be avoided. Thus, damage may be reduced to a minimum level, but is sufficient to induce a heat mediated change to the morphology of the ciliary body. This increases the dimension of the supraciliary space allowing for greater absorption of fluid, which results in decreased intraocular pressure and/or destruction of portions of the ciliary epithelium, which reduces the production of aqueous humor resulting in a reduction of intraocular pressure (IOP). FIG. 9 illustrates an exemplary pulsed mode that may be used in the embodiments herein. The illustrated mode may have an "on" time of 100 μs and an "off" time of 1900 μs with a period of 2000 μs.

Figure 10:
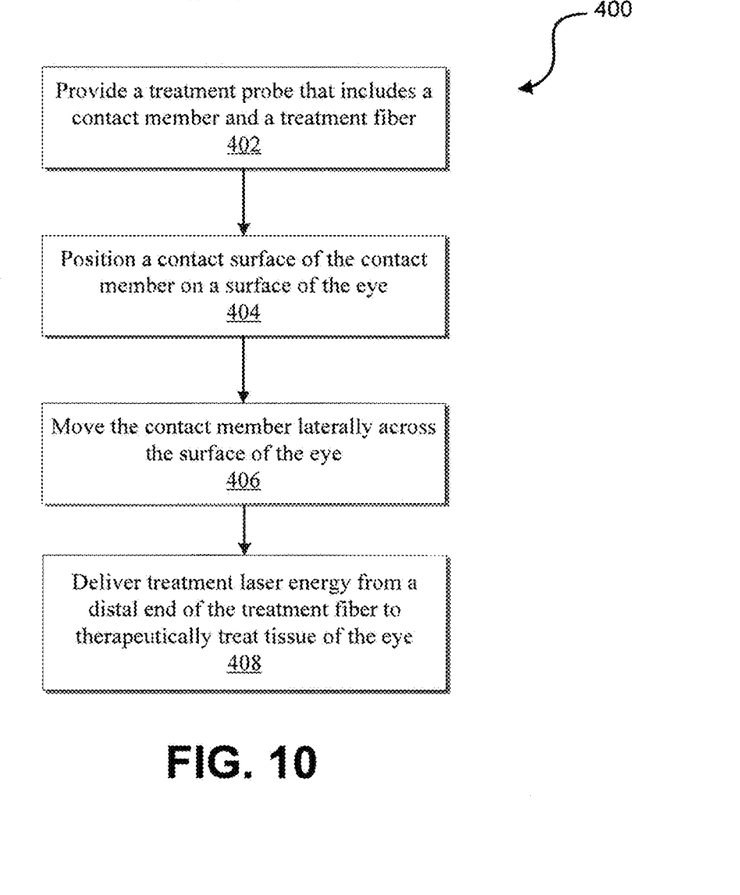
FIG. 10 illustrates a method of treating an eye of a patient.

FIG. 10 illustrates a method 400 of treating an eye of a patient. At block 402, a treatment probe is provided. The treatment probe includes an elongate body having a proximal end and a distal end and a treatment fiber that is housed in the elongate body. The treatment probe includes a contact member that is disposed on the distal end of the elongate body. The contact member includes a contact surface, two side edges that are positioned on opposite sides of the contact surface, and a fluid channel. At block 404, the contact surface is positioned on a surface of the eye. At block 406, the contact member is moved laterally across the surface of the eye. At block 408, treatment laser energy is delivered from a distal end of the treatment fiber to treat tissue of the eye. The contact surface conforms to the shape of the eye's sclera and the two side edges are shaped to direct fluid that is present on the surface of the eye toward the fluid channel as the contact member is moved laterally across the surface of the eye. The fluid is directed toward the fluid channel in order to aggregate or collect the fluid within the fluid channel and thereby wet the distal end of the treatment fiber with the fluid.

The method may be performed to treat the ciliary process of the eye with the treatment laser energy. In some embodiments, the method also includes applying an irrigation fluid to the surface of the eye. In such embodiments, the fluid that is directed toward the fluid channel includes the irrigation fluid and may also include natural tear or fluid that is produced by the eye. In some embodiments, a plurality of pulses of the laser energy may be delivered to the target tissue to induce a therapeutic response without coagulating the tissue of the eye. The plurality of pulses may be delivered while the contact member is moved laterally across the surface of the eye or while the contact member is held stationary about the eye.

In some embodiments, the method may further include positioning the contact surface on the surface of the eye so that the treatment probe is oriented angularly offset from an optical axis of the eye. In such embodiments, the treatment laser energy may be delivered angularly offset from the optical axis. In some embodiments, a reference structure of the contact surface may be positioned in alignment with a reference feature of the eye. The reference feature of the eye may be the limbus and the reference structure of the contact surface may be an edge that is separated from the distal end of the treatment fiber by between 1.5 mm and 4 mm, and more commonly 2 mm or 3 mm.

The two side edges of the contact member may be angled or tapered toward the fluid channel so that a width of the contact surface is narrowest adjacent the fluid channel. In a specific embodiment, the contact surface may have an hourglass or bowtie configuration that is configured to funnel the fluid toward the fluid channel to aggregate the fluid within the fluid channel. The contact member typically has a top end and a bottom end that are positioned on opposite ends of the two side edges and the top end typically has a greater width than the bottom end.

The distal end of the treatment fiber may be centered within the fluid channel so that the distal end of the treatment fiber is fully wettable by the fluid aggregated within the fluid channel. The fluid channel may have an axial depth from the contact surface of between 25 and 200 μm.

In some embodiments, the method may additionally include delivering the treatment laser energy through a fiber taper element that is coupled with the distal end of the treatment fiber. The treatment laser energy may be delivered through the fiber taper to reduce a divergence angle of a laser beam that is emitted from the treatment fiber. The fiber taper element may have a larger egress diameter than an ingress diameter. The ingress diameter may be between about 50 and 100 μm and the egress diameter may be between about 600 and 1000 μm. The fiber taper element may have a conical frustum shape.

While several embodiments and arrangements of various components are described herein, it should be understood that the various components and/or combination of components described in the various embodiments may be modified, rearranged, changed, adjusted, and the like. For example, the arrangement of components in any of the described embodiments may be adjusted or rearranged and/or the various described components may be employed in any of the embodiments in which they are not currently described or employed. As such, it should be realized that the various embodiments are not limited to the specific arrangement and/or component structures described herein.

In addition, it is to be understood that any workable combination of the features and elements disclosed herein is also considered to be disclosed. Additionally, any time a feature is not discussed with regard in an embodiment in this disclosure, a person of skill in the art is hereby put on notice that some embodiments of the invention may implicitly and specifically exclude such features, thereby providing support for negative claim limitations.

Having described several embodiments, it will be recognized by those of skill in the art that various modifications, alternative constructions, and equivalents may be used without departing from the spirit of the invention. Additionally, a number of well-known processes and elements have not been described in order to avoid unnecessarily obscuring the present invention. Accordingly, the above description should not be taken as limiting the scope of the invention.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included.

As used herein and in the appended claims, the singular forms "a", "an", and "the" include plural referents unless the context clearly dictates otherwise. Thus, for example, reference to "a process" includes a plurality of such processes and reference to "the device" includes reference to one or more devices and equivalents thereof known to those skilled in the art, and so forth.

What is claimed is:

1. A treatment probe for treating an eye of a patient, the eye having, a sclera, the treatment probe comprising:
   an elongate body defining a handle having a proximal end and a distal end;
   a treatment fiber housed in the elongate body and configured for delivering treatment light energy to the eye from a distal end of the treatment fiber; and
   a contact member disposed on an end of the elongate body, the contact member including:
     a contact surface for positioning on a surface of the eye;
     two side edges that are positioned on opposite sides of the contact surface; and
     a fluid channel;
   wherein the contact surface conforms to the shape of the sclera and the two side edges are shaped to direct fluid on the surface of the eye toward the fluid channel when the contact member is moved laterally across the surface of the eye such that the fluid aggregates within the fluid channel and contacts the distal end of the treatment fiber.

2. The treatment probe of claim 1, wherein the two side edges of the contact member are angled or tapered toward the fluid channel so that a width of the contact surface is narrowest adjacent the fluid channel.

3. The treatment probe of claim 2, wherein the contact surface has an hourglass or bowtie configuration that is configured to funnel the fluid toward the fluid channel to aggregate the fluid within the fluid channel.

4. The treatment probe of claim 3, wherein the contact member has a top end and a bottom end that are positioned on opposite ends of the two side edges, and wherein the lop end has a greater width than the bottom end.

5. The treatment probe of claim 1, wherein the distal end of the treatment fiber is centered within the fluid channel.

6. The treatment probe of claim 1, wherein the fluid channel has an axial depth from the contact surface of between 3 μm and 300 μm.

7. The treatment probe of claim 1, wherein the distal end of the treatment fiber includes an angle cut that is configured to bend the treatment light energy toward the eye so that the treatment light energy is delivered more perpendicularly to the eye.

8. The treatment probe of claim 1, further comprising a fiber taper element that is coupled with the distal end of the treatment fiber, the fiber taper element having a larger egress diameter than an ingress diameter and the fiber taper element being configured to reduce a divergence angle of a light beam that is emitted from the treatment fiber.

9. The treatment probe of claim 8, wherein the fiber taper element has a conical frustum shape.

10. The treatment probe of claim 8, wherein the ingress diameter is between about 50 and 100 μm and the egress diameter is between about 600 and 1000 μm.

11. The treatment probe of claim 1, wherein the contact surface comprises a reference structure that is alignable with a reference feature of the eye.

12. The treatment probe of claim 11, wherein the reference feature of the eye comprises a limbus, and wherein the reference structure of the contact surface comprises an edge separated from the distal end of the treatment fiber by between 1.5 mm and 4.0 mm.

13. The treatment probe of claim 1, wherein the eye has an optical axis, and wherein the treatment probe is configured so that when the contact surface is positioned on the surface of the eye, the treatment probe is oriented angularly offset from the optical axis of the eye and the treatment light energy is delivered angularly offset from the optical axis.

14. The treatment probe of claim 1, wherein the treatment probe is configured to deliver a plurality of pulses of the light energy to the eye to induce a therapeutic response without coagulating tissue of the eye.

15. The treatment probe of claim 1, wherein the treatment light energy is a laser beam.

16. The treatment probe of claim 1, wherein the treatment light energy is a light emitting diode (LED).

17. A method of treating an eye of a patient, the eye having a sclera, the method probe comprising:
providing a treatment probe comprising:
an elongate body having a proximal end and a distal end;
a treatment fiber housed in the elongate body; and
a contact member disposed on an end of the elongate body, the contact member including a contact surface, two side edges that are positioned on opposite sides of the contact surface, and a fluid channel;
positioning the contact surface of the contact member on a surface of the eye;
moving the contact member laterally across the surface of the eye; and
delivering treatment light energy from a distal end of the treatment fiber to treat tissue of the eye;
wherein the contact surface conforms to the shape of the sclera and the two side edges are shaped to direct fluid on the surface of the eye toward the fluid channel as the contact member is moved laterally across the surface of the eye in order to aggregate fluid within the fluid channel and thereby wet the distal end of the treatment fiber with the fluid.

18. The method of claim 17, further comprising treating a ciliary process of the eye with the treatment light energy.

19. The method of claim 17, further comprising applying an irrigation fluid to the surface of the eye, wherein the fluid that is directed toward the fluid channel includes the irrigation fluid.

20. The method of claim 17, wherein delivering treatment light energy from the distal end of the treatment fiber comprises delivering a plurality of pulses of the light energy so as to induce a therapeutic response without coagulating the tissue of the eye.

21. The method of claim 20, wherein the plurality of pulses are delivered while the contact member is moved laterally across the surface of the eye.

22. The method of claim 17, wherein the eye has an optical axis, and wherein the method further comprises positioning the contact surface on the surface of the eye so that the treatment probe is oriented angularly offset from the optical axis and the treatment light energy is delivered angularly offset from the optical axis.

23. The method of claim 17, wherein positioning the contact surface on the surface of the eye comprises positioning a reference structure of the contact surface in alignment with a reference feature of the eye.

24. The method of claim 23, wherein the reference feature of the eye comprises a limbus, and wherein the reference structure of the contact surface comprises an edge separated from the distal end of the treatment fiber by between 1.5 mm and 4.0 mm.

25. The method of claim 17, wherein the two side edges of the contact member are angled or tapered toward the fluid channel so that a width of the contact surface is narrowest adjacent the fluid channel.

26. The method of claim 25, wherein the contact surface has an hourglass or bowtie configuration that is configured to funnel the fluid toward the fluid channel to aggregate the fluid within the fluid channel.

27. The method of claim 26, wherein the contact member has a top end and a bottom end that are positioned on opposite ends of the two side edges, and wherein the top end has a greater width than the bottom end.

28. The method of claim 17, wherein the distal end of the treatment fiber is centered within the fluid channel such that the distal end of the treatment fiber is fully wettable by the fluid aggregated within the fluid channel.

29. The method of claim 17, wherein the fluid channel has an axial depth from the contact surface of between 3 µm and 300 µm.

30. The method of claim 17, further comprising delivering the treatment light energy through an angle cut of the distal end of the treatment fiber to bend the treatment light energy away from an axis of the treatment fiber and toward the eye.

31. The method of claim 17, further comprising delivering the treatment light energy through a fiber taper element that is coupled with the distal end of the treatment fiber to reduce a divergence angle of a light beam that is emitted from the treatment fiber, wherein the fiber taper element has a larger egress diameter than an ingress diameter.

32. The method of claim 31, wherein the fiber taper element has a conical frustum shape.

33. The method of claim 31, wherein the ingress diameter is between about 50 and 100 µm and the egress diameter is between about 600 and 1000 µm.

* * * * *